(12) United States Patent
Szekeres et al.

(10) Patent No.: US 11,208,383 B2
(45) Date of Patent: Dec. 28, 2021

(54) KCNQ POTENTIATORS

(71) Applicant: Eli Lilly and Company, Indianapolis, IN (US)

(72) Inventors: Helen Jane Szekeres, Bisley (GB); Maria Ann Whatton, Basingstoke (GB); Andrew Caerwyn Williams, Woodley (GB)

(73) Assignee: Eli Lilly and Company, Indianapolis, IN (US)

(*) Notice: Subject to any disclaimer, the term of this patent is extended or adjusted under 35 U.S.C. 154(b) by 142 days.

(21) Appl. No.: 16/781,148

(22) Filed: Feb. 4, 2020

(65) Prior Publication Data
US 2020/0247752 A1 Aug. 6, 2020

Related U.S. Application Data

(60) Provisional application No. 62/801,716, filed on Feb. 6, 2019, provisional application No. 62/811,038, filed on Feb. 27, 2019.

(51) Int. Cl.
*C07D 213/38* (2006.01)
*C07D 213/64* (2006.01)
*A61P 25/28* (2006.01)

(52) U.S. Cl.
CPC .......... *C07D 213/38* (2013.01); *A61P 25/28* (2018.01); *C07D 213/64* (2013.01)

(58) Field of Classification Search
CPC ...... C07D 213/38; C07D 213/64; A61P 25/28
See application file for complete search history.

(56) References Cited

U.S. PATENT DOCUMENTS 9,676,757 B2 * 6/2017 Sherer ............... A61P 25/00

FOREIGN PATENT DOCUMENTS

| CN | 103709097 | 4/2014 |
|---|---|---|
| EP | 3210969 | 8/2017 |
| WO | 2015130905 | 9/2015 |

OTHER PUBLICATIONS

Anonymous. Polarimetry, Apr. 1, 2016. Retrieved from the Internet: url:http://www.chem.ucla.edu/~cacher/General/30BL/tips/Polarimetry.html.
Bastin, R.J., et al. "Salt Selection and Optimization Procedures for Pharmaceutical New Chemical Entities," Organic Process Research and Development, 4: 427-435 (2000).
Berge, S. M., et al., "Pharmaceutical Salts," Journal of Pharmaceutical Sciences, 66: 1-19, (1977).
Berger T.A.; "Supercritical Fluid Chromatography" Primer. Agilent Technologies, Jul. 2015.
Chambers, S. M., et al. "Highly efficient neural conversion of human ES and iPS cells by dual inhibition of SMAD signaling." Nature biotechnology 27.3 (2009): 275.
Cho, B. T., et al. "Application of optically active 1, 2-diol monotosylates for synthesis of ß-azido and ß-amino alcohols with very high enantiomeric purity. Synthesis of enantiopure (R)-octopamine,(R)-tembamide and (R)-aegeline." Tetrahedron: Asymmetry 13.11 (2002): 1209-1217.
Fleckenstein et al., "Activation of axonal Kv7 channels in human peripheral nerve by flupirtine but not placebo-therapeutic potential for peripheral neuropathies: results of a randomised controlled trial," Journal of Translational Medicine 2013, 11:34.
Ghezzi, F. et al. "Functional up-regulation of the M-current by retigabine contrasts hyperexcitability and excitotoxicity on rat hypoglossal motoneurons." The Journal of physiology 596.13 (2018): 2611-2629.
Gould, P.L., "Salt selection for basic drugs," International Journal of Pharmaceutics, 33:201-217 (1986).
Hochbaum, D. R., et al. "All-optical electrophysiology in mammalian neurons using engineered microbial rhodopsins " Nature methods 11.8 (2014): 825.
International Searching Authority, International Search Report and Written Opinion for application PCT/US2020/016499, dated Apr. 15, 2020.
Kalappa, B. I., et al. "Potent KCNQ2/3-specific channel activator suppresses in vivo epileptic activity and prevents the development of tinnitus." Journal of Neuroscience 35.23 (2015): 8829-8842.
Kanai, K., et al. "Altered axonal excitability properties in amyotrophic lateral sclerosis: impaired potassium channel function related to disease stage." Brain 129.4 (2006): 953-962.
Kanai, K., et al. "Motor axonal excitability properties are strong predictors for survival in amyotrophic lateral sclerosis." J Neurol Neurosurg Psychiatry 83.7 (2012): 734-738.
Kovalchuk, et al., "Acute Effects of Riluzole and Retigabine on Axonal Excitability in Patients With Amyotrophic Lateral Sclerosis: A Randomized, Double-Blind, Placebo-Controlled, Crossover Trial," Clinical Pharmacology & Therapeutics, 104, 1136-1145 (2018).
Küçükali et al., "Peripheral nerve hyperexcitability syndromes" Rev Neurosci. 2015;26(2):239-51.
Menon, P., et al. "Cortical hyperexcitability and disease spread in amyotrophic lateral sclerosis." European journal of neurology 24.6 (2017): 816-824.
Schaus, S. E., et al. "Highly selective hydrolytic kinetic resolution of terminal epoxides catalyzed by chiral (salen) CoIII complexes. Practical synthesis of enantioenriched terminal epoxides and 1, 2-diols." Journal of the American Chemical Society 124.7 (2002): 1307-1315.
Sittl et al. "The Kv7 potassium channel activator flupirtine affects clinical excitability parameters of myelinated axons in isolated rat sural nerve," Journal of the Peripheral Nervous System 15:63-72 (2010).

(Continued)

*Primary Examiner* — Timothy R Rozof
(74) *Attorney, Agent, or Firm* — Goodwin Procter LLP

(57) ABSTRACT

Small molecule potentiatiors to potassium channels (such as Kv7 potentiators—which are also called KCNQ potentiators), compositions including such compounds, and methods of using such compounds for the treatment of Amyotrophic Lateral Sclerosis and other neurological diseases caused by changes in motor neuron excitability, including, but not limited to, primary lateral sclerosis, pseudobulbar palsy, progressive bulbar palsy, progressive muscular atrophy and epilepsy.

20 Claims, No Drawings

(56) References Cited

OTHER PUBLICATIONS

Verma, et al., "Atypical Motor Neuron Disease and Related Motor Syndromes," Seminars in Neurology, vol. 21, No. 2, 2001.
Wainger, B. J., et al. "Intrinsic membrane hyperexcitability of amyotrophic lateral sclerosis patient-derived motor neurons." Cell reports 7.1 (2014): 1-11.
Werley, C. A., et al. "All-Optical Electrophysiology for Disease Modeling and Pharmacological Characterization of Neurons." Current protocols in pharmacology 78.1 (2017): 11-20.
Zaczek, et al., "Two New Potent Neurotransmitter Release Enhancers, 10,10-Bis(4-Pyridinylmethyl)-9(10H)-Anthracenone and 10,10-Bis(2-Fluoro-4-Pyridinylmethyl)-9(10H)-Anthracenone: Comparison to Linopirdine" The Journal of Pharmacology and Experimental Therapeutics, 285:724-730, 1998.
Zheng, et al., "Activation of peripheral KCNQ channels relieves gout pain," Pain, 156 (2015) 1025-1035.

\* cited by examiner

KCNQ POTENTIATORS

The present invention is in the field of medicine. Particularly, the present invention relates to compounds, methods, and pharmaceutical compositions for treating Amyotrophic Lateral Sclerosis (ALS) and other neurological diseases caused by changes in motor neuron excitability, including, but not limited to, primary lateral sclerosis, pseudobulbar palsy, progressive bulbar palsy, progressive muscular atrophy and epilepsy.

ALS (sometimes called "Lou Gehrig's Disease") is a fatal neurological disease affecting approximately 1.5-3 in 100,000 people per year. It is characterized by progressive loss of motor neurons, typically leading to death within 2-3 years from diagnosis. Although research continues, the majority of ALS cases appear to be sporadic without a known cause.

ALS patients typically present with increased excitability of peripheral and central motor neurons, leading to fasciculations, muscle cramps and spasticity. It is thought that the increased neuronal excitability leads to calcium overload and cell death. Indeed, motor neuron excitability was negatively correlated with survival in ALS patients (See K. Kanai et. al., *J. Neurol. Neurosurg. Psychiatry*, 83, 734-738 (2012)).

Studies have investigated the mechanism and cause as to why motor neurons in ALS patients have altered excitability (as compared to non-ALS patients). (See K. Kanai et. al., *Brain*, 129, 953-962 (2006)). Results of the study suggest reduced potassium channel activity in the neurons as a major contributor to disease-associated hyperexcitability (See id.). Further, motor neurons derived from pluripotent stem cells from ALS patients have also exhibited hyperexcitability. (See B. J. Wainger et al., *Cell Rep.*, 7, 1-11 (2014)). These stem cell derived neurons displayed reduced delayed-rectifier potassium currents, and, in fact, when agents retigabine and flupirtine (which are known Kv7 potassium channel potentiators) were added to these stem cell-derived neurons, the hyperexcitability of the motor neurons was normalized and the in vitro survival of the cells increased (See id.). In another study, the Kv7 potentiator retigabine reduced symptoms of excitotoxicity and increased survival in an in vitro model of ALS using rat hypoglossal motor neurons (See F. Ghezzi et. al., *J. Physiol.*, 596, 2611-2629 (2018)).

Currently, the only drug approved to treat ALS is riluzole, which has been shown to increase survival by 2-3 months. There is clearly a need for more efficacious, better and longer-lasting treatments.

The known Kv7 potentiator retigabine acts on the Kv7.2-7.5 (KCNQ2-KCNQ5) potassium channels. It was approved as adjunct therapy in patients with drug-resistant epilepsy. It was approved in Europe and the United States in 2011, but withdrawn voluntarily in 2017. Withdrawal of retigabine from clinical use was believed to be based on a number of tolerability issues leading to very limited use of the drug. Tolerability issues include the common and presumably mechanism-based occurrence of drowsiness and dizziness and less common incidences of urinary retention and pigmentation changes in the retina and skin. Retinal changes, and the potential for vision loss, resulted in a boxed warning on the label for retigabine, and are not thought to be mechanism based. Urinary retention is most likely the result of potentiation of bladder Kv7.3/7.5 channels. However, given its side-effects, new Kv7 potentiators need to be developed.

A recent study, comparing the effects of riluzole (e.g., the approved treatment for ALS) and retigabine on motor neuron excitability in ALS patients, suggests that potentiators of Kv7 channels may have efficacy superior to riluzole (See M. Kovalchuk et. al., *Clinical Pharmacology & Therapeutics*, 104, 1136-1145 (2018)). Thus, improved potentiators, which have better tolerability than retigabine would be beneficial for clinical treatment of ALS and other hyperexcitability-related disorders. (See B. Kalappa, et al., *The Journal of Neuroscience*, 35(23):8829-8842) (2015). To date, no agents acting on Kv7 have been approved for the treatment of ALS, and thus, there remains a need for agents acting on Kv7, such as alternative Kv7 potentiators that provide a therapeutic benefit. Further, it may be beneficial to have such potentiators be more selective for Kv7.2/7.3 over other Kv7 channels. There is also a need for a new Kv7 agent that avoids undesirable side effects and that may provide a combination of improved pharmacological properties, including safety, potency, efficacy, and tolerability, in particular for the treatment of excitability of peripheral and central motor neurons.

The present embodiments provide compounds that are potassium channel potentiators (such as Kv7 potentiators—also called KCNQ potentiators) that are useful in the treatment of ALS and other neurological diseases caused by changes in motor neuron excitability.

Specifically, compounds of the following formula (which is designated as "FORMULA I") may be used as Kv7 potentiators:

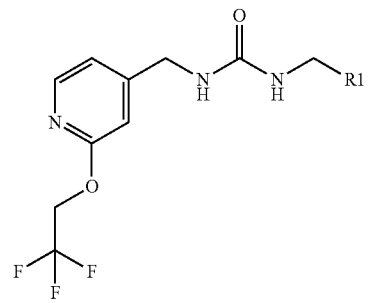

wherein R1 is

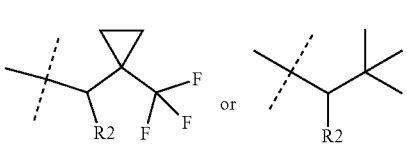

(FORMULA I)

wherein, in FORMULA I, R2 is either H or OH. In addition to the compounds for FORMULA I, one or more pharmaceutically acceptable salts may be made from the compounds of FORMULA I, and such pharmaceutically acceptable salts may also be made and used as Kv7 potentatiors.

In some embodiments the compounds of FORMULA I, or phamaceutically acceptable salts thereof, are made such that R1 is

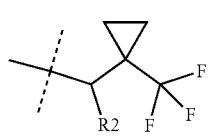

and R2 is H.

In other embodiments, the compounds of FORMULA I (or phamaceutically acceptable salts thereof) are made such that R1 is

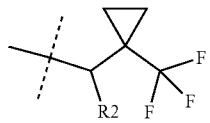

and R2 is OH. Moreover, in such embodiments, when R2 is OH, the carbon to which the OH group is attached is a stereocenter. Accordingly, in some embodiments, the compounds (or phamaceutically acceptable salts) of FORMULA I may be the racemic mixture of the two enantiomers. In other embodiments, a particular enantiomer may be used, including either of the following enantiomers:

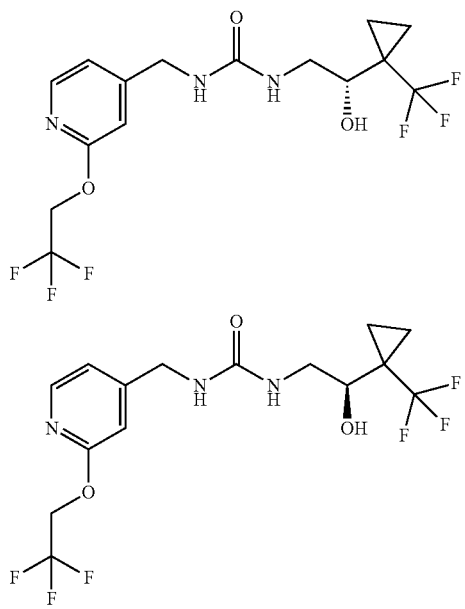

Those skilled in the art will appreciate how to construct embodiments which use only one of the foregoing enantiomers. Other embodiments may be designed with mixtures of the different enantiomers having different percentages for each component.

In other embodiments the compounds of FORMULA I (or phamaceutically acceptable salts thereof) are made such that R1 is

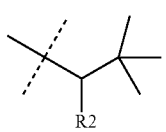

and R2 is H.

In yet additional embodiments, the compounds of FORMULA I (or phamaceutically acceptable salts thereof) are made such that R1 is

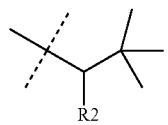

and R2 is OH. Moreover, in such embodiments, when R2 is OH, the carbon to which the OH group is attached is a stereocenter. Accordingly, in some embodiments, the compounds (or phamaceutically acceptable salts) of FORMULA I may be the racemic mixture of the two enantiomers. In other embodiments, a particular enantiomer may be used, including either of the following enantiomers:

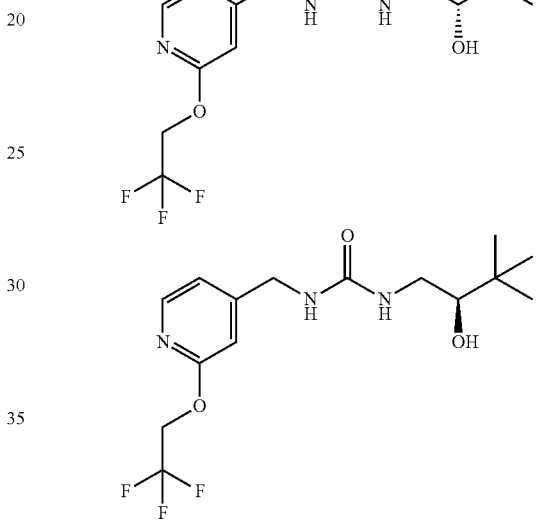

Those skilled in the art will appreciate how to construct embodiments which use only one of the foregoing enantionmers. Other embodiments may be designed with mixtures of the different enantiomers having different percentages for each component.

The present embodiments further provide pharmaceutical compositions comprising a compound or pharmaceutically acceptable salt of FORMULA I and one or more pharmaceutically acceptable carriers, diluents or excipients. Such pharmaceutical compositions may provide a method of treating a disease. Specifically, the present embodiments provide a method for treating a disease caused by changes in motor neuron excitability comprising administering to a patient in need thereof an effective amount of a compound of FORMULA I (or pharmaceutically acceptable salt thereof). In some particularly preferred embodiments, the disease caused by changes in motor neuron excitability is ALS.

Other embodiments provide a method of treating a disease caused by changes in motor neuron excitability comprising administering to a patient in need thereof an effective amount of a compound of FORMULA I (or a pharmaceutically acceptable salt thereof). In some particularly preferred embodiments, the disease caused by changes in motor neuron excitability is ALS.

The present embodiments also provides the compounds of FORMULA I (or pharmaceutically acceptable salts thereof)

for use in therapy. More particularly, the present embodiments provide a compound of FORMULA I (or a pharmaceutically acceptable salt thereof) for use in the treatment of a disease caused by changes in motor neuron excitability. In some embodiments, such a disease may be ALS.

Further, the present embodiments provide the use of a compound of FORMULA I (or pharmaceutically acceptable salts thereof) in the manufacture of a medicament for the treatment of a disease caused by changes in motor neuron excitability. In some such embodiments, the disease is ALS.

As used herein, the term "disease associated with changes in motor neuron excitability" or a "disease caused by changes in motor neuron excitability" include a disease selected from the group consisting of ALS, primary lateral sclerosis, pseudobulbar palsy, progressive bulbar palsy, epilepsy and progressive muscular atrophy. These terms also include all of the diseases listed in A. Verma, et al., "Atypical Motor Neuron Disease and Related Motor Syndromes," *Seminars in Neurology, Volume* 21, Number 2, 2001. Such terms also include PNH (peripheral nerve hyper excitability) disorders. Information about PNH disorders can be found at C. Küçükali et al., "Peripheral nerve hyperexcitability syndromes" *Rev Neurosci.* 2015,26(2):239-51. Accordingly, the compounds and pharmaceutically acceptable salts herein may be used to treat one or more of these diseases.

As used interchangeably herein, the term "patient," "subject," and "individual," refers to a human, a more particularly, a patient in need thereof. In certain embodiments, the patient is further characterized with a disease, disorder, or condition (e.g., ALS or another disease) that would benefit from a potentiation of Kv7. In another embodiment, the patient is further characterized as being at risk of developing a condition described above, or condition that would benefit from potentiation of Kv7.

An effective amount can be determined by one skilled in the art by the use of known techniques and by observing results obtained under analogous circumstances. In determining the effective amount for a patient, a number of factors are considered, including, but not limited to: its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. An effective amount, in some embodiments, provides a clinically significant reduction in the excitability of peripheral and central motor neurons.

The compounds of the present invention are formulated as pharmaceutical compositions administered by any route which makes the compound bioavailable. Preferably, such compositions are for oral administration. Such pharmaceutical compositions and processes for preparing the same are well known in the art (See, e.g., Remington: The Science and Practice of Pharmacy, L. V. Allen, Editor, 22$^{nd}$ Edition, Pharmaceutical Press, 2012).

The compounds of FORMULA I and the pharmaceutically acceptable salts thereof are particularly useful in the treatment methods of the invention, with certain configurations being preferred. The following list of compounds of the present invention describe such configurations. It will be understood that these preferences are applicable both to the treatment methods and to the compounds of the invention.

Compounds of the present embodiments (in which R2 is OH) include:

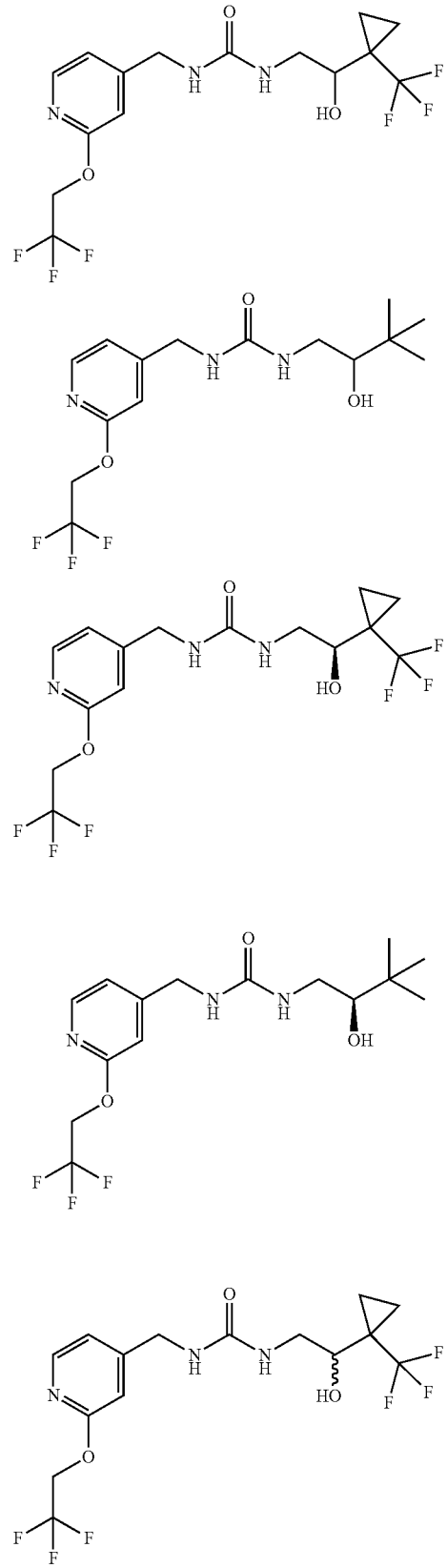

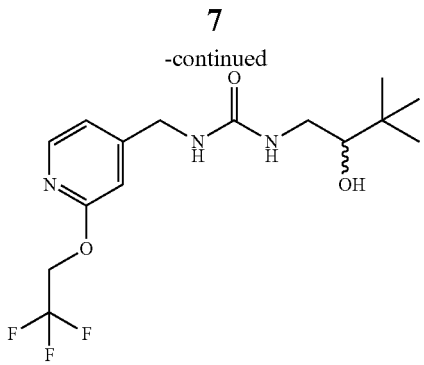

In these compounds in which R2 is OH, compounds with the "flat bond" above are racemic and/or have both enantiomers present (either in a 50/50 mixture or at some other ratio). Compounds with the wedged and dashed bond above depict the particular enantiomer. Compounds with the "wavy" bond indicate that it is single enantiomer present, but the exact configuration of this single enantiomer is unknown, and thus, such enantiomers are distinguished by their optical rotation (e.g., whether they rotate light in the (+) or (−) direction.)

Compounds of the present embodiments also include the following molecules (in which R2 is H):

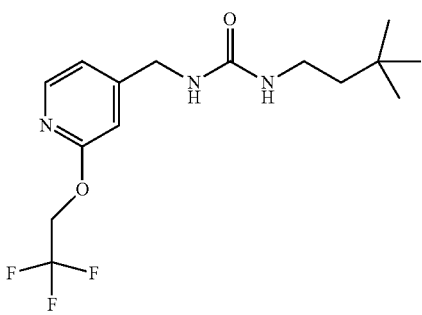

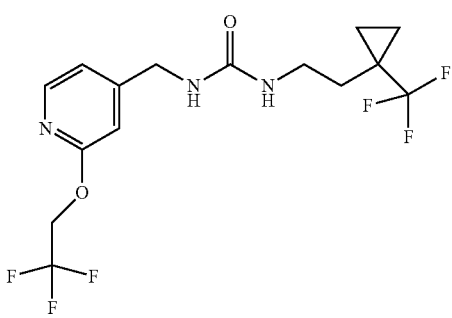

Compounds above that have an OH group as R2 may be those that have the OH in the "up" configuration (as indicated by the wedged projection). Other embodiments may be designed in which the OH group is in the "down" configuration. Those skilled in the art will appreciate how to make this other enantiomer, for example, by using a different starting materials and/or using different reactions, etc. Such enantiomers have the following structure and are part of the presently claimed embodiments:

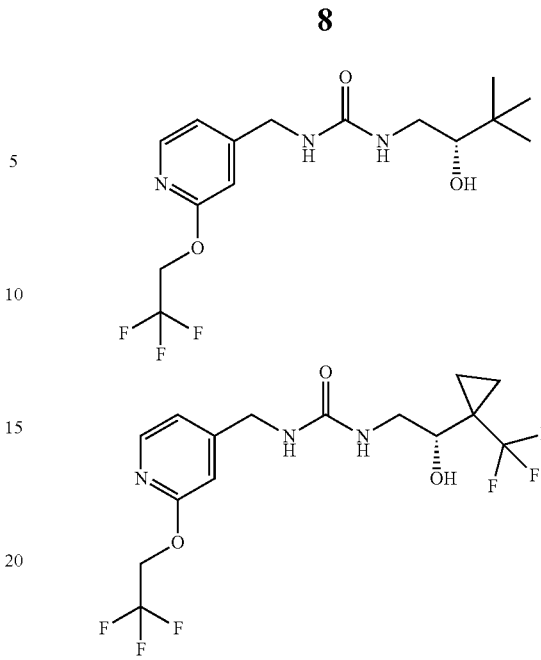

Although the present invention contemplates all individual enantiomers and diasteromers, as well as mixtures of the enantiomers of said compounds, including racemates, the above-recited compounds and pharmaceutically acceptable salts thereof are particularly preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate aspects of the invention. In addition, one of ordinary skill in the art appreciates that compounds of FORMULA I may be prepared by using starting material or intermediate with the corresponding desired stereochemical configuration which can be prepared by one of skill in the art.

Certain abbreviations may be used below. These abbreviations mean as follows: "ACN" refers to acetonitrile; "Ac" refers to acetyl; "AcOH" refers to acetic acid; "Ac$_2$O" refers to acetic anhydride; "AP5" refers to (2R)-amino-5-phosphonopentanoate; "BDNF" refers to Brain-derived neurotrophic factor; "BOC" refers to tert-butoxycarbonyl, "CAS #" refers to Chemical Abstracts Registry number; "CMAP" refers to compound muscle action potential; "DCM" refers to methylene chloride or dichloromethane; "DIPEA" refers to N,N-diisopropylethylamine; "DMEA" refers to dimethylethylamine; "DMF" refers to N,N-dimethylformamide; "DMSO" refers to dimethyl sulfoxide; "D-PBS" refers to Dulbecco's phosphate buffered Saline; "EDTA" refers to ethylenediaminetetraacetic acid; "EGTA" refers to ethylene glycol-bis(β-aminoethyl ether)-N,N,N',N'-tetraacetic acid; "ES/MS" refers to Electrospray Mass Spectrometry; "Et$_2$O" refers to diethyl ether; "EtOAc" refers to ethyl acetate; "EtOH" refers to ethanol or ethyl alcohol; "h" refers to hour or hours; "HEPES" refers to 4-(2-hydroxyethyl)-1-piperazineethanesulfonic acid "IPA" refers to isopropanol or isopropyl alcohol; "IPAm" refers to isopropyl amine; "iPrOAc" refers to isopropyl acetate; "LC/MSMS" refers to Liquid Chromatography with tandem mass spectrometry; "LiHMDS" refers to lithium bis(trimethylsilyl)amide; "KOtBu" refers to potassium-tert-butoxide, "Me" refers to methyl; "msec" refers to millisecond or milliseconds as a unit of time; "MTBE" refers to methyl-tert-butyl ether; "min" refers to minute or minutes; "NaOtBu" refers to sodium-tert-butoxide, "n-BuLi" refers to n-butyllithium; "NBQX" refers to (2,3-dihydroxy-6-nitro-7-sulfamoyl-benzo[f]quinoxaline; "OAc" refers to acetate or acetoxy; "PBS" refers to phosphate-buffered saline; "RT" refers to room temperature; "SCX" refers to strong cation exchange; "SD" refers to standard deviation; "sec" refers to second or seconds as a unit of time; "SEM" refers to Standard Error of the Mean; "SFC" refers to Supercritical Fluid Chromatography; "TEA" refers to triethylamine; "TFA" refers to trifluoroacetic acid; "THF" refers to tetrahydrofuran; "TMA" refers to trimethylamine; "TMEDA" refers to tetramethylethylenediamine; "Tris" refers to tris(hydroxymethyl)aminomethane or 2-amino-2-(hydroxymethyl)propane-1,3-diol, "[α]$_D^{20}$" refers to specific optical rotation at 20° C. and 589 nm, wherein c is the concentration in g/mL (which is usually g/100 mL).

General Schemes

Scheme 1

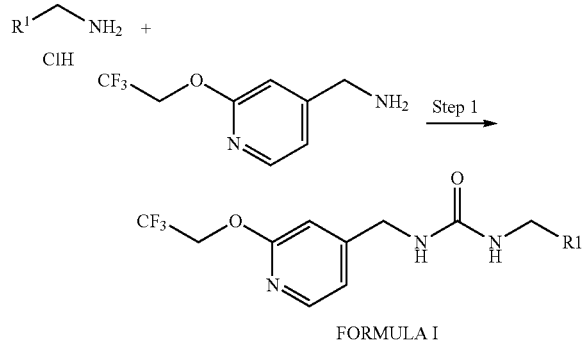

FORMULA I

Scheme 1 illustrates the preparation of compounds of FORMULA I, wherein R$^1$ is defined as described above. Activated ester formation of an appropriately substituted amine (or its corresponding salt, e.g., HCl) is well documented in the art, using, for example, carbonyldiimidazole, and selective N-vs. O-carbonylation of (2-ethoxy-4-pyridyl)methanamine (or its corresponding salt form, e.g., HCl) with said activated intermediate with an suitable organic base may yield the desired ureas of the present invention (Step 1). The skilled artisan will recognize that compounds or FORMULA I containing stereochemistry may be prepared via a chirally-substituted amine to obtain a single enantiomer, or by chiral resolution of the compound of FORMULA I, using either chiral chromatography techniques, such as SFC, or by the use of a chiral auxiliary, such as a chiral salt preparation, as is well known in the art.

Scheme 2

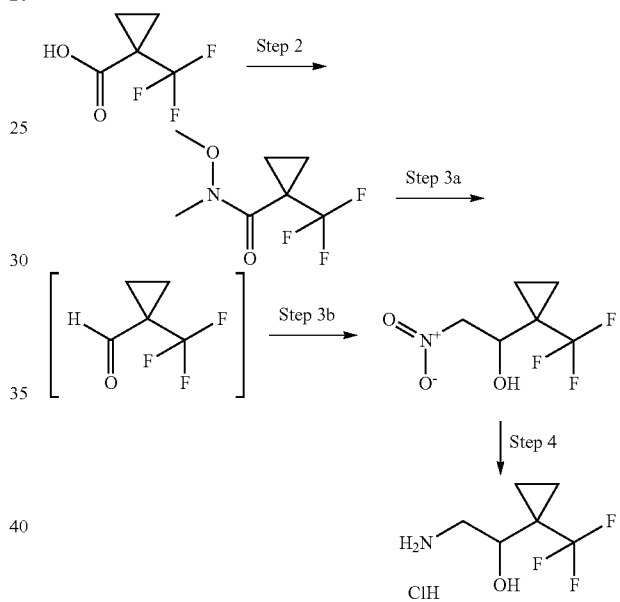

Scheme 2 depicts the preparation of rac-2-amino-1-[1-(trifluoromethyl)-cyclopropyl]ethanol hydrochloride. Weinreb-type amide preparation (Step 2) from (trifluoromethyl)cyclopropanecarboxylic acid may be accomplished under a variety of conditions well described in the art. A two step process to prepare nitro-1-[1-(trifluoromethyl)cyclopropyl]ethanol via reduction of the Weinreb-type amide with standard reducing agents (Step 3a), using, for example, lithium aluminum hydride in a suitable organic solvent, such as THF or Et$_2$O, followed by isolation of the aldehyde and addition of the anion of nitromethane, generated in the presence of a strong base, such as NaH or KOtBu, to the corresponding aldehyde (Step 3b), may give the desired racemic 2-nitro-1 [1-(trifluoromethyl)cyclopropyl]ethanol. Subsequent reduction of the nitro group (Step 4) to the corresponding amine may be accomplished under a variety of conditions well described in the art, and the resulting amine may be converted to an appropriate salt form, e.g., HCl, for ease of use. The skilled artisan will recognize that the racemic mixture of the amine may be resolved into its two chiral enantiomers using standard techniques well known in the art, such as chiral chromatography, or preparation using a chiral salt auxiliary.

Scheme 3

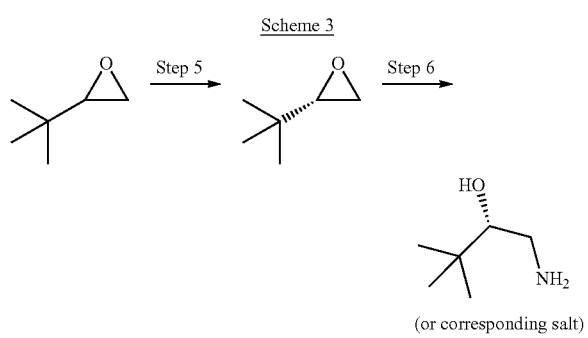

(or corresponding salt)

Scheme 3 depicts the preparation of the requisite (2S)-1-amino-3,3-dimethyl-butan-2-ol or its corresponding salt. Kinetic resolution of 2-tert-butyloxirane (Step 5) using a chiral transition-metal catalyst, such as $Co^{2+}$ which has been activated to $Co^{3+}$, may be achieved based on the literature reported in *JACS* 9 VOL. 124, NO. 7, 2002, 1307. Resultant stereochemistry may be assigned depending on the stereochemistry of the chiral catalyst. Hence, (2S)-2-tert-butyloxirane may be prepared using S,S-(salen)$Co^{3+}$OAc (see *JACS* 9 VOL. 124, NO. 7, 2002, 1307). Additionally, verification of the S-stereochemistry may be accomplished by comparison to reported data in *Tetrahedron: Asymmetry* 13 (2002) 1209-1217. Stereocontrolled epoxide ring-opening may be achieved using a nitrogen nucleophile, such as $NH_3$ in MeOH, under conditions well known to the skilled artisan (Step 6). The resulting amino alcohol may be converted to a suitable salt form under well known conditions in the art.

Preparation 1

N-methoxy-N-methyl-1-(trifluoromethyl)cyclopropanecarboxamide

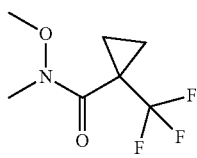

Cool a mixture of commercially available 1-(trifluoromethyl)cyclopropanecarboxylic acid [CAS #277756-46-4] (4.8 g, 31.4 mmol) and N,O-dimethylhydroxylamine hydrochloride (4.65 g, 46.7 mmol) in EtOAc (50 mL) to 0° C. and add a solution of 2,4,6-tripropyl-1,3,5,2,4,6-trioxatriphosphorane-2,4,6-trioxide solution (50 mass % in DMF, 28 mL, 47.5 mmol) dropwise via addition funnel. Stir the reaction mixture at RT for 20 h. Cool the reaction mixture to 0° C. and quench by pouring into saturated aqueous $NH_4Cl$ solution. Separate the resulting phases and extract the aqueous layer with EtOAc. Combine the organic extracts, dry over $MgSO_4$, filter, and evaporate to dryness to give the title compound (4.4 g, 67% yield). $^1H$ NMR (400 MHz, $CDCl_3$) δ 3.74 (s, 3H), 3.29 (s, 3H), 1.33-1.25 (m, 4H). ES/MS: m/z 198 [M+H].

Preparation 2

(±)-2-nitro-1-[1-(trifluoromethyl)cyclopropyl]ethanol

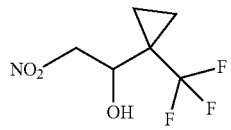

Add a 1M solution of lithium aluminum hydride in THF (20 mL, 20 mmol) to a 0° C. solution of N-methoxy-N-methyl-1-(trifluoromethyl)cyclopropanecarboxamide (4.3 g, 20.9 mmol) in $Et_2O$ (50 mL) dropwise and stir the resulting mixture for 1 h. Quench the reaction by dropwise addition of water (0.81 mL), then 2 M aqueous NaOH (0.81 mL) and then additional water (2.43 mL). Add $MgSO_4$ (5 g) and filter the resulting mixture through a pad of diatomaceous earth with minimal vacuum to give, what is believed to be, a solution of 1-(trifluoromethyl)cyclopropanecarbaldehyde in $Et_2O$. Add this solution dropwise to a rapidly stirring solution of nitromethane (60 mL, 1.1 mol) and KOtBu (360 mg, 3.17 mmol) at 0° C. After ~1 h, warm the reaction to RT and stir overnight. Decant the solvent from the brown gum in the flask and concentrate under reduced pressure. Purify the resulting residue on silica gel, eluting 0-10% MeOH/DCM, to give the title compound as a colourless oil (2.9 g, 67% yield). $^1H$ NMR (400 MHz, $CDCl_3$) δ 0.97-0.91 (m, 1H), 1.13-0.99 (m, 3H), 2.66 (d, J=5.1 Hz, 1H), 4.41-4.36 (ddd, J=9.8, 5.1, 2.4 Hz, 1H), 4.59-4.53 (dd, J=9.8, 13.8 Hz, 1H), 4.68 (dd, J=2.4, 13.8 Hz, 1H).

Preparation 3

(±)-2-amino-1-[1-(trifluoromethyl)cyclopropyl]ethanol hydrochloride

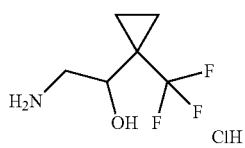

Add a 1 M solution of lithium aluminum hydride in THF (37 mL, 37 mmol) to a 0° C. solution of (±)-2-nitro-1-[1-(trifluoromethyl)cyclopropyl]ethanol (2.9 g, 14.8 mmol) in $Et_2O$ (30 mL) dropwise and stir the resulting reaction mixture to RT overnight. Cool the mixture to 0° C. and add additional 1M solution of lithium aluminium hydride in THF (15 mL, 15 mmol) dropwise. Warm the reaction mixture to RT and stir for 4 h. Quench the reaction mixture at 0° C. by dropwise addition of water (1.96 mL), then 2 M aqueous NaOH (1.96 mL), and then water (5.88 mL). Add $MgSO_4$ (5 g), stir the resulting mixture for 10 min, and filter through a bed of diatomaceous earth. Treat the filtrate with 4 M HCl in dioxane (20 mL, 80 mmol) and concentrate under reduced pressure. Suspend the resulting residue in $Et_2O$ (50 mL) with rapid stirring. Isolate the resulting white solid by filtration to give the title compound (1.52 g, 47% yield). ES/MS: m/z=170 [M+H].

Alternative Procedure for Preparation 3

To a PARR flask add Platinum (IV) oxide (242 mg, 1.07 mmol), a solution of (±)-2-nitro-1[1-(trifluoromethyl)cyclopropyl]ethanol (2.42 g, 11.5 mmol) in EtOH (24 mL) and Acetic acid (4.96 mL). Place the flask under a Hydrogen atmosphere at 55 psi and shake for 5 h at RT. Filter the reaction through a bed of diatomaceous earth and concentrate under reduced pressure. Slurry the residue in 1,4-Dioxane (17.2 mL) and add 4N HCl in 1,4-Dioxane (10 mL, 40 mmol) dropwise and stir for 2 h. Filter the mixture and wash the cake with 1,4-Dioxane and pull dry under vacuum for 15 minutes. Dry the resultant solid in a vacuum oven at 45° C. for 3 h to give the title compound (2.21 g, 80% yield).

Preparation 4 (which Gives Example 2)

(±)-1-[2-hydroxy-2-[1-(trifluoromethyl)cyclopropyl]ethyl]-3-[[2-(2,2-trifluoroethoxy)-4-pyridyl]methyl]urea

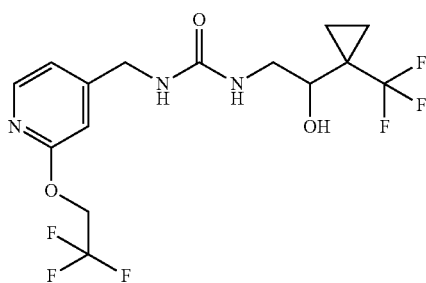 [SMILES: O=C(NCc1ccnc(OCC(F)(F)F)c1)NCC(O)C1(C(F)(F)F)CC1]

Cool a suspension of [2-(2,2,2-trifluoroethoxy)-4-pyridyl]methanamine hydrochloride [CAS #2044704-69-8] (200 mg, 0.8 mmol) in DCM (4 mL) to 0° C., add DIPEA (580 µL, 3.3 mmol) and 1,1'-carbonyldiimidazole (149 mg, 0.9 mmol). Stir the resulting reaction vigorously at 0° C. for 15 min and add (±)-2-amino-1-[1-(trifluoromethyl)cyclopropyl]ethanol hydrochloride (232 mg, 1.01 mmol). Stir the resulting mixture at RT overnight. Quench by the addition of water, dilute with DCM, and pass through a hydrophobic frit. Evaporate the organic layers and purify the resulting residue on silica gel, eluting with 0-15% MeOH/DCM, to give the title compound (198 mg, 57% yield). ES/MS: m/z=402 [M+H].

Alternative Procedure for Preparation 4

Stir [2-(2,2,2-trifluoroethoxy)-4-pyridyl]methanamine dihydrochloride (500 mg, 1.79 mmol) and DIPEA (1.26 mL, 7.16 mmol) in DCM (10 mL) to give a clear solution. Add 1,1'-carbonyldiimidazole (311 mg, 1.88 mmol) and stir 30 minutes. Add (±)-2-amino-1-[1-(trifluoromethyl)cyclopropyl]ethanol hydrochloride (465 mg, 2.15 mmol) and stir the reaction at RT for 48 h. Add water, separate the organic phase and dry over sodium sulphate. Filter and evaporate the organics and purify the resulting residue on silica gel, eluting 0-15% MeOH/DCM, to give the title compound (680 mg, 90% yield).

The chiral portion of this molecule may be synthesised using kinetic resolution and ring opening chemistry.

Preparation 5

(2S)-1-amino-3,3-dimethyl-butan-2-ol hydrochloride

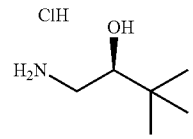

Obtain (2S)-2-tert-butyloxirane commercially (CAS #40102-55-4) or via a kinetic resolution as reported in J. AM. CHEM. SOC. 9 VOL. 124, NO. 7, 2002 1307 wherein its reported that the R configured epoxide is obtained from the RR catalyst, hence the S epoxide is obtained from the SS catalyst:

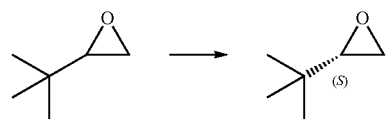

Heat a mixture of (2S)-2-tert-butyloxirane (107 g, 1.01 moles) and NH$_4$OH (1.3 L, 10.7 moles) in EtOH (427 mL) in a sealed vessel at 100° C. for 4 h. Cool and concentrate under reduced pressure. Dissolve the resulting residue in DCM (100 mL) at 0° C. and add a 4 M solution of HCl in dioxane (267 mL, 1.1 moles) slowly over 10 min while a white precipitate forms. Filter the resulting solid, wash with cold DCM, and dry by vacuum suction to give the title compound (103 g; 62.9% yield). $^1$H NMR (300.1 MHz, MeOD): δ 0.94 (s, 9H), 2.76 (dd, J=11.1, 12.6 Hz, 1 H), 3.09 (dd, J=2.5, 12.6 Hz, 1 H), 3.41 (dd, J=2.5, 11.1 Hz, 1 H). $[\alpha]_D^{20}$=+32.38° (c=0.8 g/100 mL, EtOH). Literature reported in *Tetrahedron: Asymmetry* 13 (2002) 1209-1217 $[\alpha]_D^{20}$=+25.9° (c=0.47 g/100 mL, EtOH).

Alternative Procedure for Preparation 5

Prepare two ISCO 2-1000 ml syringe pumps labeled A and B:

Fill Pump A with a 7 M solution of NH$_3$ in MeOH. Fill Pump B with a solution of (2S)-2-tert-butyloxirane (25 g, 232 mmol) dissolved in a 7 M solution of NH$_3$ in MeOH (995 mL). Connect the pumps to a 500 mL stainless steel tube reactor (OD=⅛") in an oven, then connect to the outlet, a 7 mL stainless steel tube reactor (OD=1/16") located outside the oven to act as a heat exchanger, and connect an EQUILIBAR® back pressure regulator set at 1200 psi after the heat exchanger.

Using pump A, fill the tube reactor with 7 M solution of NH$_3$ in MeOH at 5 mL/min. Set oven temperature at 200° C. Once the tube reactors are full, switch to pump B at 10 mL/min for 100 min and then switch to pump A to deliver 7 M solution of NH3 in MeOH at the same flow rate for 1 additional h.

Concentrate the collected solution under reduced pressure at RT to give crude (2S)-1-amino-3,3-dimethyl-butan-2-ol (24.4 g). Dissolve the crude material in tert-butyl methyl ether (150 mL) and add a 5.5 M solution of HCl in IPA (46.4 mL, 255 mmol) drop wise over 5 min with vigourous stirring. Filter the resulting white solid, wash with MTBE (4×25 mL), and dry to give the title compound (23 g, 72% yield).

Preparation 6

[2-(2,2,2-trifluoroethoxy)-4-pyridyl]methanamine dihydrochloride

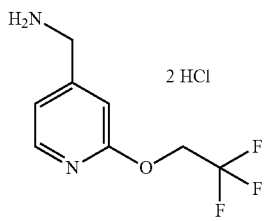 [SMILES: NCc1ccnc(OCC(F)(F)F)c1]

Stir 2-(2,2,2-trifluoroethoxy)pyridine-4-carbonitrile [CAS #618446-30-3] 82.5 g, 367 mmol) in EtOH (500 mL), decant the solution from the undissolved solid, and wash the solid with EtOH (3×50 mL) decanting the solution each time. Combine the EtOH solutions, dilute with additional EtOH (150 mL), and add an aqueous solution of conc. HCl (125 mL). Add a slurry of 10% palladium on carbon (3.7 g) in about 10 mL EtOH. Shake the resulting reaction mixture under an atmosphere of $H_2$ at 60 psi at RT overnight. Filter the mixture through pad of diatomaceous earth, washing with EtOH, and concentrate the filtrate under reduced pressure to leave a white solid. Slurry the resulting solid in MTBE at 45° C. for 30 min, cool the mixture to RT, and filter to give a solid. Dissolve the solid in water (400 mL) and extract twice with MTBE (400 then 200 ml). Concentrate the aqueous phase under reduced pressure to give a cream colored solid which is slurried in THF (100 mL) and filtered. The filter cake is washed with THF (2×30 ml) and dried under vacuum suction to give the title compound (46.16 g, 44% yield). The filtrate is additionally concentrated under reduced pressure and dried in a vacuum oven overnight. The resulting solid is slurried in THF (50 mL) for 30 min and filtered to give an additional crop of the title compound (34 g, 32.5% yield). ES/MS: m/z 307 [M+H]. Chloride ion analysis (IC) showed molar ratio 2:1 chloride ion:Parent.

EXAMPLE 1

1-[(2S)-2-hydroxy-3,3-dimethyl-butyl]-3-[[2-(2,2,2-trifluoroethoxy)-4-pyridyl]methyl]urea

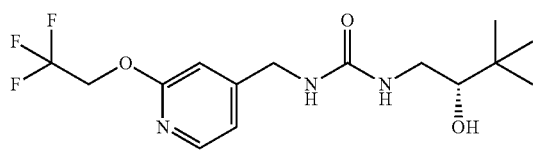 [SMILES: CC(C)(C)[C@H](O)CNC(=O)NCc1ccnc(OCC(F)(F)F)c1]

Stir [2-(2,2,2-trifluoroethoxy)-4-pyridyl]methanamine hydrochloride (8.06 g, 33.2 mmol) in DCM (50 mL) and add DIPEA (29 mL, 166 mmol). Stir the resulting mixture for 5 min and add 1,1'-carbonyldiimidazole (5.7 g, 33.2 mmol). Stir the mixture for 10 min and add (2S)-1-amino-3,3-dimethyl-butan-2-ol hydrochloride (5 g, 32.5 mmol) and stir the resulting reaction mixture over the weekend. Wash the reaction mixture with water, separate the organic phase, and concentrate under reduced pressure. Purify the resulting residue by flash column chromatography on silica gel, eluting with 0 to 10% MeOH in DCM, to give the title compound (8.16 g, 72% yield) after solvent evaporation.

Combine material with another lot of the title compound (4.37 g) prepared as described above and recrystallize from iPrOAc (45 ml) to give 11.29 g of the title compound. ES/MS: m/z 350 [M+H]. $[\alpha]_D^{20}$=+29.845° (c=0.2 g/100 mL, MeOH).

EXAMPLE 2

(+)-1-[2-hydroxy-2-[1-(trifluoromethyl)cyclopropyl]ethyl]-3-[[2-(2,2,2-trifluoroethoxy)-4-pyridyl]methyl]urea and (−)1-[2-hydroxy-2-[1-(trifluoromethyl)cyclopropyl]ethyl]-3-[[2-(2,2,2-trifluoroethoxy)-4-pyridyl]methyl]urea via Chiral Resolution

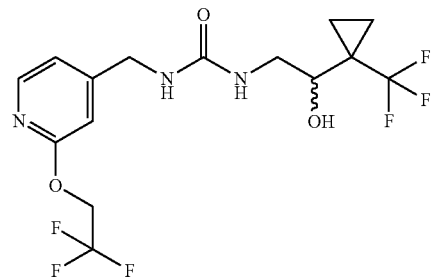 [SMILES: O=C(NCc1ccnc(OCC(F)(F)F)c1)NCC(O)C1(C(F)(F)F)CC1]

Subject (±)-1-[2-hydroxy-2-[1-(trifluoromethyl)cyclopropyl]ethyl]-3-[[2-(2,2,2-trifluoroethoxy)-4-pyridyl]methyl]urea (680 mg) to SFC chiral purification using a CHIRALPAK® AD-H (250×30 mm, 5μ column at 35° C., 100 bar, eluting 92:8 $CO_2$/ethanol with 0.2% N,N-dimethylethylamine @152 mL/min and detection at 220 nm, evaporate fractions and dry in a 45° C. vacuum oven to give:

Enantiomer 1 ($1^{st}$ eluting peak, 285.4 mg): (−)-1-[2-hydroxy-2-[1-(trifluoromethyl)cyclopropyl]ethyl]-3-[[2-(2,2,2-trifluoroethoxy)-4-pyridyl]methyl]urea, $[\alpha]_D^{20}$=−21.0° (c=0.20 g/100 mL, MeOH), Enantiomer 2 ($2^{nd}$ eluting peak, 289.5 mg). Subject enantiomer 2 to SFC purification a second time using the method described above; evaporate fractions and dry in a 45° C. vacuum oven to give (+)-1-[2-hydroxy-2-[1-(trifluoromethyl)cyclopropyl]ethyl]-3-[[2-(2,2,2-trifluoroethoxy)-4-pyridyl]methyl]urea (236 mg); $[\alpha]_D^{20}$=+15.0° (c=0.20 g/100 mL, MeOH).

EXAMPLE 3

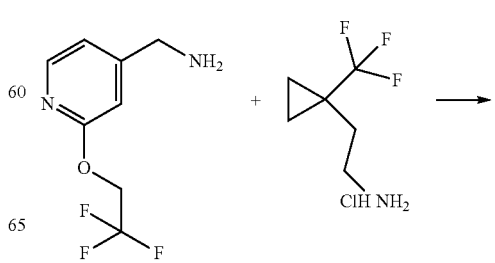

-continued

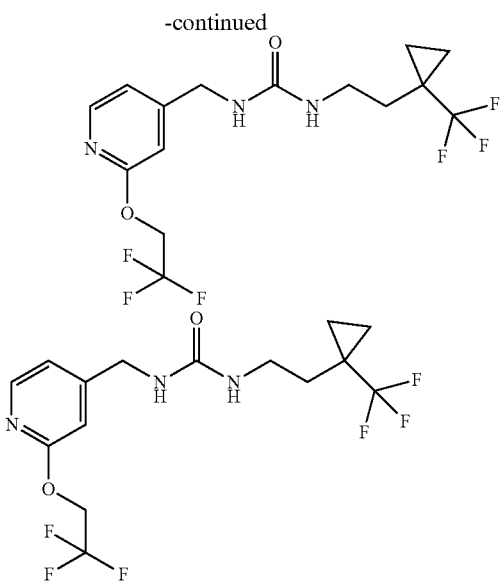

1-[[2-(2,2,2-trifluoroethoxy)-4-pyridyl]methyl]-3-[2-[1-(trifluoromethyl)cyclopropyl]ethyl]urea In a round bottomed flask, stir 2-[1-(trifluoromethyl)cyclopropyl]ethanamine hydrochloride (500 mg, 2.6 mmol; see WO 2013/134252 but also commercially available [CAS #: 1454690-80-2]) in DCM (5 mL) and add DIPEA (1.4 mL, 8 mmol). When a clear solution results add 1,1'-carbonyldiimidazole (428 mg, 2.6 mmol) and stir the resulting mixture at RT for 30 min. Add [2-(2,2,2-trifluoroethoxy)-4-pyridyl]methanamine dihydrochloride (810 mg, 2.9 mmol) in a single portion and stir at room temperature for 30 min. Warm the reaction to 40° C. for 3 h and stir at RT for 16 h. Transfer the reaction to a microwave vial and heat at 100° C. for 30 min. Purify the resulting mixture by silica gel chromatography, eluting with 0-10% MeOH in DCM, to give the title compound (892 mg, 88% yield). ES/MS: m/z 386 [M+H]

Alternate Procedure for Example 3

To a microwave reaction vessel add commercially available 2-[1-(trifluoromethyl)cyclopropyl]ethanamine hydrochloride (758 mg, 0.4 mmol, CAS #561297-93-6), DCM (2 mL), DIPEA (698 µL, 0.4 mmol) and 1,1'-carbonyldiimidazole (649 mg, 0.4 mmol). Shake at RT for 5 h. Add a 0.5 M prepared solution of commercially available [2-(2,2,2-trifluoroethoxy)-4-pyridyl]methanamine (CAS #1454690-80-2; alternately, see WO 2013/134252) in DCM (0.8 mL, 0.4 mmol) at RT. Heat the resulting mixture in microwave at 100° C. for 30 min. Decant the reaction mixture into a larger round bottom flask and dilute with water (5 mL) and DCM (5 mL). Stir for 15 min at RT and pass through a hydrophobic frit to separate the organic phase. Concentrate the filtrate under reduced pressure and purify the resulting residue by high pH reverse phase chromatography, using a 75×30 mm PHENOMENEX® GEMINI®-NX C18 column, 5µ particle size, 110A, AXIA column with GEMINI®-NX C18 15×30 mm guard, eluting with 23-57% of ACN in 10 mM NH$_4$HCO$_3$ (pH-10) containing 5% MeOH as the aqueous phase, to give 1-[[2-(2,2,2-trifluoroethoxy)-4-pyridyl]ethyl]-3-[2-1-(trifluoromethyl)cyclopropyl]ethyl]urea (90.6 mg, 59% yield). ES/MS: m/z 386 [M+H]

Assays

Biological assay data showing that the compounds of the present embodiments are active in potentiating Kv7 is provided below.

Assay #1

Optopatch Excitability Assay for Example 1 in Motor Neurons Derived From ALS Patient iPSC Lines Altered excitability of cortical neurons and lower motor neuron is an important factor in the pathophysiology of ALS (See, for example, K. Kanai, et. al., *J Neurol Neurosurg Psychiatry*, 83, 734-738 (2012); P. Menon, et. al., *Eur J Neurol.*, 24, 816-824 (2017)). All-optical electrophysiology ("Optopatch") was used to evaluate excitability in cultured motor neurons derived from iPSC lines from two ALS patients with different pathogenic mutations.

Cell Culture: The two iPSC lines are derived from one patient with a pathogenic mutation in TARDBP and one patient with a pathogenic repeat expansion mutation in C9orf72, respectively. Motor neurons are generated from these lines by a 2D differentiation method adapted from the dual SMAD inhibition neuronal patterning protocol (See S. M. Chambers, et. al., *Nat Biotechnol.*, 27, 275-280 (2009)) by inclusion of motor neuron morphogens. Differentiation is verified by visual inspection, karyotyping and staining for beta-III-tubulin and the nuclear motor neuron marker ISL1. Neurons are cultured on a monolayer of mouse glia in mTeSR (Stem Cell Technologies), supplemented with 10 ng/mL BDNF. Forty-eight hours prior to imaging, 100 nM trans-retinal was added to the medium.

Transduction with Optopatch vectors: At 15 days in vitro, cultured motor neurons are transduced with a lentiviral vector to drive the co-expression of the actuator CheRiff-mOrange2 and the voltage indicator QuasAr3-Citrine (for details see D. R. Hochbaum, et. al., *Nat. Methods*, 11, 825-833 (2014)). Forty-eight hours prior to imaging, 100 nM trans-retinal was added to the medium.

Solutions: Recordings are performed in Brainphys™ imaging buffer with 3 mM potassium. The gap junction blocker 2-aminoethoxydiphenyl borate (50 µM) is added to eliminate electrical coupling between cells, and NBQX (10 µM), gabazine (20 µM), and AP5 (25 µM) were used to block synaptic transmission.

Optopatch Recordings: Five days after transduction, Optopatch imaging is performed on a custom, ultra-wide-field fluorescence microscope at RT. Motor neurons are illuminated with red laser excitation (200 W/cm$^2$; 635 nm) to monitor changes in QuasAr fluorescence and blue LED excitation (0-127 mW/cm$^2$, 470 nm) to depolarize the cell membrane with CheRiff. A custom blue light stimulus protocol is used consisting of: i) 2 sec of red illumination only to monitor spontaneous activity, ii) 5×500 msec steps of increasing blue light intensity and iii) 2×2 sec linearly increasing blue light ramps, each with a different maximum blue intensity. Optopatch data are recorded using a Hamamatsu ORCA-Flash 4.0 sCMOS camera with a 1 kHz frame rate. The field of view size is 4 mm×0.5 mm. Custom control software written in MATLAB is used to control illumination protocols and record all movies. To examine acute effects of Kv7.2/7.3 potentiators, neurons are incubated with test compound for 15 min prior to imaging.

Data Analysis: Image segmentation analysis is performed using temporal Principle Component Analysis and spatial-temporal Independent Component Analysis to isolate individual neurons. A spike-finding algorithm is used to find action potentials, and data are analyzed for compound effects on mean firing rate, adaptation, rheobase and action potential waveform shape by comparing to vehicle controls (for detail, see C. A. Werley, et. al., *Curr. Protoc. Pharmacol.*, 78, 11.20.1-11.20.24. (2017)).

Subjected to the protocol described above, the primary effect of the Example 1 is on the action potential firing rate in response to low intensity blue light illumination. At a blue LED illumination intensity of 5.1 mW/cm$^2$, the compound decreased action potential frequency in a concentration-dependent manner.

Fitting a 4-parameter logistic equation to the data may be used to determine the potency ($EC_{50}$) of the effect of Example 1 on action potential frequency. Results are shown in Table 1 for two separate differentiation efforts each for the lines derived from the patients carrying the TARDBP and C9orf72 mutations. The observed effects are qualitatively similar but more potent that those seen with the known Kv7.2/7.3 potentiator flupirtine, demonstrating the potential utility of Example 1 for treating ALS by reducing excitability of patient-derived motor neurons.

TABLE 1

Inhibition of excitability in ALS patient derived motor neurons (presented as mean (95% confidence interval))

|  | TARDBP | | C9orf72 | |
| --- | --- | --- | --- | --- |
|  | Diff 1 | Diff 2 | Diff 1 | Diff 2 |
| Example 1 $EC_{50}$ (μM) | 0.15 (0.05, 0.25) | 0.15 (0.06, 0.24) | 0.17 (0.09, 0.25) | 0.20 (0.14, 0.25) |
| Flupirtine $EC_{50}$ (μM) | 1.15 (0.65, 1.66) | 0.84 (0.48, 1.21) | 1.66 (1.31, 2.01) | 1.35 (0.82, 1.88) |

Assay #2

Modulation of Kv7.2/7.3 Conductance by Kv7 Potentiators in a Mammalian Expression System The potency and efficacy of Kv7 potentiators is assessed by automated electrophysiology on the IonWorks Barracuda (Molecular Devices) platform using the population patch clamp mode of the instrument.

Cell Culture: HEK293 cells stably expressing hKv7.2 (under tetracycline induction) and hKv7.3 (Catalog #CT6147, Charles River) are used for these studies. Cells are maintained in a Dulbecco's modified Eagle's medium/nutrient mixture Ham's F-12 (Sigma-Aldrich) supplemented with 5% tetracycline-screened fetal bovine serum (Sigma-Aldrich), 15 mM HEPES, 500 μg/mL G418, 100 U/mL penicillin, 100 μg/mL streptomycin, 29.2 mg/mL L-glutamine, 100 μg/mL zeocin, and 5 μg/mL blasticidin. Expression of hKv7.2 is induced by addition of 1 μg/mL doxycycline 24 h prior to recordings.

Cells are cultured in Corning T-150 flasks to a confluence of 85%-95%. At the start of an experiment, cells are washed once with D-PBS without calcium and magnesium and then dissociated by incubating in 3 ml of 0.25% trypsin for 8 min at 37° C. Cells ware resuspended in media, triturated gently, and centrifuged for 4 min at 1,000 rpm. Cells are resuspended in external solution to a final concentration of 2.5-3.5M cells/mL.

Solutions: External solution wis composed of (in mM): 140 NaCl, 5 KCl, 2 CaCl$_2$, 1 MgCl$_2$, 10 HEPES, 10 Glucose, pH 7.4. Internal solution is composed of (in mM): 90 K-gluconate, 40 KCl, 3.2 EGTA, 3.2 MgCl$_2$, 5 HEPES, pH 7.25. The membrane perforating agent amphotericin B is prepared daily as a 27 mg/mL stock solution in DMSO and then added to the internal solution to a final concentration of 0.1 mg/mL. Test article dilutions are prepared in 384-well plates from 10 mM DMSO stock solutions and diluted using acoustic dispensing (Labcyte ECHO®), such that final DMSO concentrations are 0.1%.

Electrophysiological Recordings: Resuspended cells are placed on the IONWORKS® BARRACUDA™ (IWB) instrument, external solution is added to a 384-well patch plate, and a hole test is performed to determine blocked wells and offset voltages. Cells are then added to the patch plate (9 μL per well) by the instrument. Two seal tests are performed prior to introducing the perforating agent amphotericin in the internal solution and allowing approximately 8 min to obtain electrical access, which is verified by a third seal test. The command voltage protocol consists of a family of 1 sec voltages steps from −80 mV to +40 mV from a holding potential of −80 mV and is applied prior to (baseline) and 6 min after test article addition.

Data Analysis: Data are acquired and leak subtracted using IWB software. Current amplitudes during the last 10 msec of each voltage step are averaged and exported. Further analysis is performed using Microsoft Excel and GraphPad Prism. Current amplitude is converted to conductance (G) by the following formula: G=I/(V-Ek) where I=current, V=step potential, Ek=potassium reversal potential (−84 mV). Conductance in the presence of test article is normalized to the baseline conductance at +40 mV for the same well. Conductance-voltage (G-V) curves are fitted with the Boltzmann equation y=Bottom+(Top-Bottom)/(1+EXP(($V_m$−$V_{0.5}$)/k)).

The test article-mediated shift in the mid-point of the conductance curve ($V_{0.5}$) is shown in Table 2 for Examples 1-3.

TABLE 2

Difference from control in the voltage at half-maximal conductance in the presence of varying concentrations of test compound.

| | Voltage Shift ($\Delta V_{0.5}$) | | | | | |
| --- | --- | --- | --- | --- | --- | --- |
| | Example 1 | | Example 2 | | Example 3 | |
| Concentration (μM) | Mean (n = 9) | SD | Mean (n = 2) | SD | Mean (n = 4) | SD |
| 10 | −38.0 | 3.7 | −25.8 | 6.8 | −21.9 | 1.3 |
| 3.33 | −28.0 | 5.1 | −23.0 | 4.5 | −23.9 | 1.5 |
| 1.11 | −13.2 | 3.2 | −10.6 | 6.6 | −21.9 | 1.8 |
| 0.37 | −3.5 | 4.4 | −1.9 | 4.1 | −19.6 | 4.5 |
| 0.12 | 0.0 | 3.4 | 2.9 | 3.3 | −11.0 | 2.4 |
| 0.04 | 1.3 | 2.4 | 7.4 | 5.2 | −4.4 | 2.1 |
| 0.01 | 1.6 | 2.7 | 4.1 | 3.3 | −1.8 | 0.5 |
| 0.005 | 3.0 | 2.9 | 5.0 | 1.8 | 1.9 | 1.8 |
| 0.0015 | 2.0 | 2.9 | 4.1 | 3.2 | 0.1 | 1.3 |
| 0.0005 | 2.6 | 4.4 | 6.1 | 0 | 3.9 | 1.4 |

(SD above refers to Standard Deviation).

Fitting a 4-parameter logistic equation to the data may be used to determine the potency ($EC_{50}$) and efficacy (maximal shift) for each test compound. Results are shown in Table 3 for Examples 1-3.

TABLE 3

Potency and efficacy of Kv7.2/7.3 potentiators

|  | Example 1 | Example 2 | Example 3 |
|---|---|---|---|
| $EC_{50}$ (µM) | 2.0 | 1.1 | 0.10 |
| Maximal Shift | −44 | −28 | −23 |
| Slope | 1.2 | 1.3 | 1.1 |

Assay #3

Threshold Tracking to Measure the Effects of Example 1 at 3,10 and 30 mg/kg IP on Peripheral Nerve Excitability Threshold tracking is a non-invasive technique that allows measurement of the excitability properties of peripheral axons by providing information about their membrane potential and ion channel function.

Method 16 male Wistar rats from Charles River, weighing between 307-446 g ware used. Animals are group housed with standard housing conditions (4 per cage, 07:00 h to 19:00 h light phase, constant temperature (21° C.) and humidity, and free access to food and water, as well as environmental enrichment).

Rats are anesthetized with isoflurane (2-2.5%, $O_2$ at 0.5 L/min) and then placed on their back on a heating pad to keep the tail temperature above 32° C. The placement of the ring electrodes are marked out and the marked sections of the tail are scraped with a blade to remove hair and the top layer of skin. The sites are cleaned with water and dried, allowing fora good conduction between the skin and the sticky electrodes.

A sticky ring stimulating electrode (+ve anode) is wrapped around the foot. A second sticky ring stimulating electrode (−ve cathode) is wrapped 1.5 cm from the base of the tail. A needle recording electrode is placed just off center on the top of the tail, 6 cm distal to the stimulating cathode at the base of the tail. A needle reference electrode is placed just off center on the top of the tail, 2 cm distal to the recording electrode. A sticky ground electrode is wrapped around the tail 2 cm proximal from the recording electrode.

Study Protocol

Start the Multitrack program (description below) and Spike.
Record 15 min of stable baseline
After the 15 min, dose with Example 1 or HEC
Take blood spot for PK at the following:
10 min post dose
20 min post dose
30 min post dose
40 min post dose
45 min after IP (intraperitoneal) dosing with Example 1, dose XE-991 (XE-991 is a commercially available compound that blocks KCNQ potentiator effects in a formalin assay in vivo—see Y. Zheng, et al., "Activation of peripheral KCNQ channels relieves gout pain," Pain, 156 (2015) 1025-1035; and R. Zaczek, et al., "Two New Potent Neurotransmitter Release Enhancers, 10,10-Bis(4-Pyridinylmethyl)-9(10H)-Anthracenone and 10,10-Bis(2-Fluoro-4-Pyridinylmethyl)-9(10H)-Anthracenone: Comparison to Linopirdine" *The Journal of Pharmacology and Experimental Therapeutics,* 285:724-730, 1998.

(XE-991 is only dosed after Example 1 at 30 mg/kg)
Take blood spot for PK at the following:
10 min post dose (55 min post Example 1 administration)
20 min post dose (65 min post Example 1 administration)
30 min post dose (75 min post Example 1 administration)
40 min post dose (85 min post Example 1 administration)

In threshold tracking assay to measure the excitability properties of peripheral axons studies in rat, compound is administered by IP at 3, 10 or 30 mg/kg using 1% hydroxyethylcellulose: 0.25% polysorbate 80:0.05% antifoam: purified water (HEC) formulation. Dry blood spots (DBS) are collected around 10, 20, 30 and terminal 40 min post-dose. DBS samples are dried at RT for around 2 h. Brain samples are obtained at terminal time point and frozen until analysis. DBS samples are shipped and stored at RT.

A 1-mg/mL stock solution of Example 1 is prepared and is serially diluted into pooled rat blood to prepare standards ranging from 1 to 10000 ng/mL. Blood wis spiked to blank DBS cards to make the standards. One 3 mm punch of the DBS standards or samples are added to 96 well plate and 180 µL of the internal standard (IS) in 1:1 ACN:MeOH is added. Shake for 45 min, dilute the extraction solution two fold with water, and analyze by LC/MSMS for drug concentration analysis.

Brain samples are homogenized using 1.14 mL of MeOH:$H_2O$ (2:8). Standards are prepared by spiking stock solution into a series of blank brain homogenates in the range of 5 to 50000 ng/mL. 25 µL of standard or sample are pipetted into 96 well plate and 180 µL of the internal standard (IS) in 1:1 ACN:MeOH is added and mixed. Samples are centrifuged at 4000 RPM at 4° C. for 10 min. Supernatant are diluted 15 fold with water and analyzed by LC/MSMS.

Samples and standards are analyzed with a Sciex API 4000 Triple Quadrupole Mass Spectrometer (Sciex, Division of MDS Inc., Toronto, Canada) coupled to a Shimadzu HPLC System (LC-IOAD, Shimadzu Corporation) and a Gilson 215 Autosampler. Samples (0.01 mL) are injected onto a HPLC column of 5-µm Betasil C-18, 20×2.1 mm Javelin (Thermo Electron Corp. Cat #70105-022106), and eluted with a gradient. The chromatographic conditions consist of mobile phase A of water/1M $NH_4HCO_3$ (2000:10, v/v) and mobile phase B of MeOH/1M N $NH_4HCO_3$ (2000:10, v/v) that is run over a 2.5-min gradient at a flow rate of 1.5 mL/min. A positive ion mode with turbo spray and an ion source temperature of 740° C. are utilized for mass spectrometric detection. Quantitation is performed using multiple reaction monitoring (MRM) at the following transitions: Quantitation is performed using multiple reaction monitoring (MRM) at the following transitions: Example 1 (m/z 350.2 to m/z 233.0) and an analog internal standard (m/z 263.1 to m/z 148.1). Linear regression plots of compounds to internal standard peak area ratios versus drug concentrations are derived with 1/×2 Quadratic.Linear regression plots of compounds to internal standard peak area ratios versus drug concentrations are derived with $1/x^2$ Quadratic.

The analog internal standard used is 2-(dimethylamino)-N-pentyl-3-phenyl-propanamide 2,2,2-trifluoroacetic acid (1:1) and has the following structure:

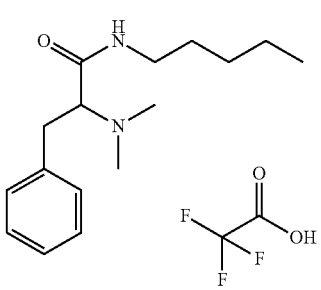 [SMILES: CCCCCNC(=O)C(Cc1ccccc1)N(C)C ; O=C(O)C(F)(F)F]

This analog internal standard purchased from Syncom, which is a company from the Netherlands with an address of Kadijk 3, 9747 AT Groningen, The Netherlands.

Drug binding to rat plasma proteins and brain homogenates is determined using in vitro dialysis method after spiking drug into these matrixes and incubated over 4.5 h at 37° C., while undergoing orbital shaking. Assay is performed using a HT dialysis micro equilibrium device and a dialysis membrane strips (MWCO 12-14k). A time 0 sample is taken after protein matrix and samples are taken from both the protein side and buffer side of the membrane after 4.5 h of incubation. Parent is quantitated by LC-MSMS at both 0 and 45 min time points. Fraction unbound is calculated by dividing the concentration of the buffer side by the concentration of the protein side. Percent recovery is also calculated by dividing the sum of the buffer and protein chambers by the time 0 concentration after 4.5 h. Unbound compound concentrations are calculated using total concentration*Fraction unbound.

Results: Effects of Example 1 on Absolute Threshold is Shown in Table 4

TABLE 4

| Compound | Dose | Unbound Exposure in Blood, nM (±SEM) | Threshold Tracking absolute threshold for 40% CMAP, % baseline (±SEM) |
| --- | --- | --- | --- |
| Example 1 | 3 mg/kg (IP) | 145 (±90) | 121 (±10) |
| Example 1 | 10 mg/kg (IP) | 193 (±50) | 140 (±8) |
| Example 1 | 30 mg/kg (IP) | 352 (±245) | 160 (±18) |

CMAP = Compound Muscle Action Potential.

(For additional information on this assay, see R. Sittl et al. "The Kv7 potassium channel activator flupirtine affects clinical excitability parameters of myelinated axons in isolated rat sural nerve," *Journal of the Peripheral Nervous System* 15:63-72 (2010); M. Kovalchuk, et al., "Acute Effects of Riluzole and Retigabine on Axonal Excitability in Patients With Amyotrophic Lateral Sclerosis: A Randomized, Double-Blind, Placebo-Controlled, Crossover Trial," Received 7 Mar. 2018; accepted 13 Apr. 2018; advance online publication 00 Month 2018. doi:10.1002/cpt.1096, *CLINICAL PHARMACOLOGY & THERAPEUTICS*, VOLUME 00 NUMBER 00, MONTH 2018; and J. Fleckenstein et al., "Activation of axonal Kv7 channels in human peripheral nerve by flupirtine but not placebo-therapeutic potential for peripheral neuropathies: results of a randomised controlled trial," *Journal of Translational Medicine* 2013, 11:34.)

There is a significant difference in time and time*treatment interaction (two-way RM ANOVA; time effect $F(26, 312)=13.18$, $p=<0.0001$; time*treatment interaction $F (78, 312)=2.888$, $p<0.0001$. A Bonferroni multiple comparisons test showed that Example 1 at 30 mg/kg significantly increased absolute threshold (decrease in excitability) compared with vehicle. XE-991 was able to reverse this increase (increase excitability).

We claim:
1. A compound of the Formula:

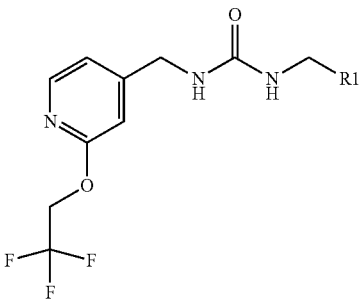

wherein R1 is

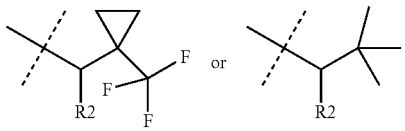

and wherein R2 is H or OH,
or a pharmaceutically acceptable salt thereof.
2. The compound according to claim 1 wherein R1 is:

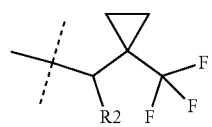

or a pharmaceutically acceptable salt thereof.
3. The compound according to claim 2, wherein R2 is OH, or a pharmaceutically acceptable salt thereof.
4. The compound according to claim 3 of the Formula:

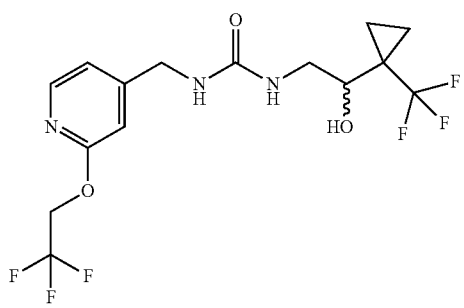 [SMILES: O=C(NCc1ccnc(OCC(F)(F)F)c1)NCC(O)C1(C(F)(F)F)CC1]

wherein the compound comprises a single enantiomer that has the (+) optical rotation in methanol, or a pharmaceutically acceptable salt thereof.

5. The compound according to claim 3 of the Formula:

wherein the compound comprises a single enantiomer that has the (−) optical rotation in methanol, or a pharmaceutically acceptable salt thereof.

6. The compound according to claim 2, wherein R2 is H, or a pharmaceutically acceptable salt thereof.

7. The compound according to claim 1, wherein R1 is or a pharmaceutically acceptable salt thereof.

8. The compound according to claim 7, wherein R2 is H, or a pharmaceutically acceptable salt thereof.

9. The compound according to claim 7, wherein R2 is OH, or a pharmaceutically acceptable salt thereof.

10. The compound according to claim 9 of the Formula:

or a pharmaceutically acceptable salt thereof.

11. The compound according to claim 9 of the Formula:

or a pharmaceutically acceptable salt thereof.

12. A pharmaceutical composition comprising a compound according to claim 1 or a pharmaceutically acceptable salt thereof, with one or more pharmaceutically acceptable carriers, diluents or excipients.

13. A method of treating a disease caused by changes in motor neuron excitability, wherein the disease is ALS, comprising administering to a patient in need thereof an effective amount of a compound according to claim 1, or a pharmaceutically acceptable salt thereof.

14. A method of treating a disease caused by changes in motor neuron excitability, wherein the disease is ALS, comprising administering to a patient in need thereof the pharmaceutical composition of claim 12.

15. A compound according to claim 1, or a pharmaceutically acceptable salt thereof, for use in therapy.

16. A compound according to claim 1, or a pharmaceutically acceptable salt thereof, for use in the treatment of a disease caused by changes in motor neuron excitability, wherein the disease is ALS.

17. A process for preparing a pharmaceutical composition, comprising admixing a compound according to claim 1, or a pharmaceutically acceptable salt thereof, with one or more pharmaceutically acceptable carriers, diluents, or excipients.

18. A compound of the Formula:

or a pharmaceutically acceptable salt thereof.

19. A compound of the Formula:

wherein the compound comprises a single enantiomer that has the (+) optical rotation in methanol, or a pharmaceutically acceptable salt thereof.

20. A compound of the Formula:

or a pharmaceutically acceptable salt thereof.

* * * * *